US012097066B2

(12) United States Patent
Maji et al.

(10) Patent No.: US 12,097,066 B2
(45) Date of Patent: Sep. 24, 2024

(54) IMAGING SYSTEM WITH BALANCED INTEGRATED POWER SOURCE

(71) Applicant: GE Precision Healthcare LLC, Wauwatosa, WI (US)

(72) Inventors: Goutam Maji, Karnataka (IN); Girish Makarabbi, Karnataka (IN); Dangashiya Dhaval Pravinbhai, Karnataka (IN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 197 days.

(21) Appl. No.: 17/654,541

(22) Filed: Mar. 11, 2022

(65) Prior Publication Data

US 2023/0284988 A1    Sep. 14, 2023

(51) Int. Cl.
*A61B 6/03*   (2006.01)
*A61B 6/00*   (2006.01)

(52) U.S. Cl.
CPC ............. *A61B 6/56* (2013.01); *A61B 6/035* (2013.01); *A61B 6/4435* (2013.01); *A61B 6/4476* (2013.01); *A61B 2560/0214* (2013.01)

(58) Field of Classification Search
None
See application file for complete search history.

(56) References Cited

U.S. PATENT DOCUMENTS

| | | | | |
|---|---|---|---|---|
| 5,448,608 A * | 9/1995 | Swain | .................... | A61B 6/035 378/20 |
| 8,218,726 B2 * | 7/2012 | Bressel | .................... | A61B 6/56 378/103 |
| 8,379,797 B2 * | 2/2013 | Abenaim | ............... | A61B 6/027 378/103 |
| 9,314,221 B2 * | 4/2016 | Katcha | ................... | A61B 6/032 |
| 9,526,461 B2 | 12/2016 | Gregerson et al. | | |
| 9,737,273 B2 * | 8/2017 | Gregerson | ........... | A61B 6/4405 |
| 10,646,192 B2 * | 5/2020 | Shanthakumar | ....... | A61B 6/032 |
| 10,835,190 B2 * | 11/2020 | Gregerson | ........... | A61B 6/4405 |
| 10,925,559 B2 * | 2/2021 | Gregerson | ............. | A61B 6/035 |

(Continued)

FOREIGN PATENT DOCUMENTS

CN   110138036 A  *  8/2019
CN   110313929 A  *  10/2019

(Continued)

OTHER PUBLICATIONS

"ZLE70103BADA—Application Development Kit for ZL70103," Microsemi Website, Available Online at https://www.microsemi.com/existing-parts/parts/139412, Available as Early as Sep. 18, 2020, 3 pages.

(Continued)

*Primary Examiner* — Thomas R Artman
(74) *Attorney, Agent, or Firm* — McCoy Russell LLP

(57) ABSTRACT

Methods and systems are provided for an imaging system including a gantry with a rotatable section including an integrated power source. The integrated power source is configured to provide power to an x-ray tube and other components coupled to the rotatable section and is configured to rotate with the rotatable section. The integrated power source is configured to provide a counter-weight to other components coupled to the rotatable section to increase a rotational balance of the gantry.

26 Claims, 4 Drawing Sheets

(56) References Cited

U.S. PATENT DOCUMENTS

| | | | |
|---|---|---|---|
| 11,311,268 B2* | 4/2022 | Nishijima | G01R 31/382 |
| 11,457,882 B2* | 10/2022 | Shizukuishi | A61B 6/56 |
| 11,559,270 B2* | 1/2023 | Gregerson | H05G 1/10 |
| 11,723,613 B2* | 8/2023 | Shizukuishi | A61B 6/0407 |
| | | | 378/15 |
| 2010/0220837 A1* | 9/2010 | Bressel | A61B 6/56 |
| | | | 378/103 |
| 2012/0027161 A1* | 2/2012 | Abenaim | A61B 6/4233 |
| | | | 378/103 |
| 2012/0256099 A1* | 10/2012 | Gregerson | A61B 6/035 |
| | | | 378/4 |
| 2014/0275953 A1* | 9/2014 | Gregerson | A61B 6/4405 |
| | | | 600/407 |
| 2015/0036786 A1* | 2/2015 | Katcha | A61B 6/56 |
| | | | 378/104 |
| 2017/0360387 A1* | 12/2017 | Gregerson | A61B 6/4405 |
| 2018/0263591 A1* | 9/2018 | Shanthakumar | H02J 9/062 |
| 2021/0022691 A1* | 1/2021 | Gregerson | A61B 6/4405 |
| 2021/0038182 A1* | 2/2021 | Nishijima | A61B 6/54 |
| 2021/0128090 A1* | 5/2021 | Gregerson | A61B 6/035 |
| 2021/0153825 A1* | 5/2021 | Shizukuishi | A61B 6/56 |
| 2023/0000450 A1* | 1/2023 | Shizukuishi | A61B 6/4241 |
| 2023/0119321 A1* | 4/2023 | Gregerson | H05G 1/10 |
| | | | 378/197 |
| 2023/0284988 A1* | 9/2023 | Maji | A61B 6/4447 |
| | | | 378/197 |

FOREIGN PATENT DOCUMENTS

| | | | | |
|---|---|---|---|---|
| CN | 111887879 A | * | 11/2020 | |
| JP | 2021023671 A | * | 2/2021 | A61B 6/032 |

OTHER PUBLICATIONS

"What is a Solenoid Switch : Working & Its Applications," Elprocus Website, Available Online at https://www.elprocus.com/what-is-a-solenoid-switch-working-its-applications/, Available as Early as Sep. 19, 2020, 7 pages.

* cited by examiner

IMAGING SYSTEM WITH BALANCED INTEGRATED POWER SOURCE

FIELD

The present description relates generally to methods and systems for medical imaging, and in particular, for computed tomography (CT) imaging with a rotatable gantry including a balanced integrated power source.

BACKGROUND/SUMMARY

Imaging systems configured for computed tomography (CT) imaging often include a slip ring configured to transfer electrical power from a stationary section of the system to an x-ray generator and other accessories coupled to a rotatable gantry. The slip ring is an electro-mechanical device that carries high electrical current while the x-ray generator is operated. However, operation of the slip ring may increase a likelihood of misalignment and/or wear of the slip ring over time, resulting in an increased maintenance frequency of the imaging system to reduce occurrences of degradation or electrical impedance of the slip ring.

According to the present disclosure, the issues described above may be addressed by a method for an imaging system, comprising: electronically coupling a motor configured to drive a rotatable section of a gantry to a stationary electrical storage device arranged at a stationary section of the gantry; and electronically coupling an x-ray tube to an integrated electrical storage device mounted to the rotatable section, where the integrated electrical storage device is selectably electronically isolated from the stationary electrical storage device.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The following description relates to systems and methods for an imaging system including a gantry having a rotatable section including a balanced integrated power source. A medical imaging system, such as the imaging system shown schematically by FIG. 1, includes a gantry including a rotatable section configured to rotate around a subject for imaging of the subject. The imaging system includes an integrated power source coupled to the rotatable section of the gantry as shown by FIGS. 2-5. As the imaging system is controlled to rotate the rotatable section of the gantry for imaging of the subject according to the methods described herein, such as the method illustrated by the flow chart of FIG. 6, the balanced integrated power source supported by the rotatable section rotates with the rotatable section. The integrated power source coupled to the rotatable section is selectably electronically couplable to a stationary power source arranged at a stationary section of the gantry, and the integrated power source may be electrically charged via the electronic coupling of the integrated power source to the stationary power source during conditions in which the rotatable section of the gantry is not rotating. By configuring the rotatable section of the gantry to include the integrated power source, the imaging system may provide imaging of the subject without a slip ring, which may reduce a manufacturing cost and/or assembly time of the imaging system. The stationary power source may be electrically charged via an external power source and may provide energization of a motor configured to drive the rotatable section, which may reduce an electrical power consumption of the imaging system. The integrated power source is configured to balance a rotation of the gantry by providing a counter-weight to other components of the imaging system such as an x-ray detector, x-ray emitter, etc. In this way, the rotatable section may rotate with a reduced likelihood of oscillation and reduced mechanical load, and an imaging quality of the imaging system may be increased.

Figure 1:
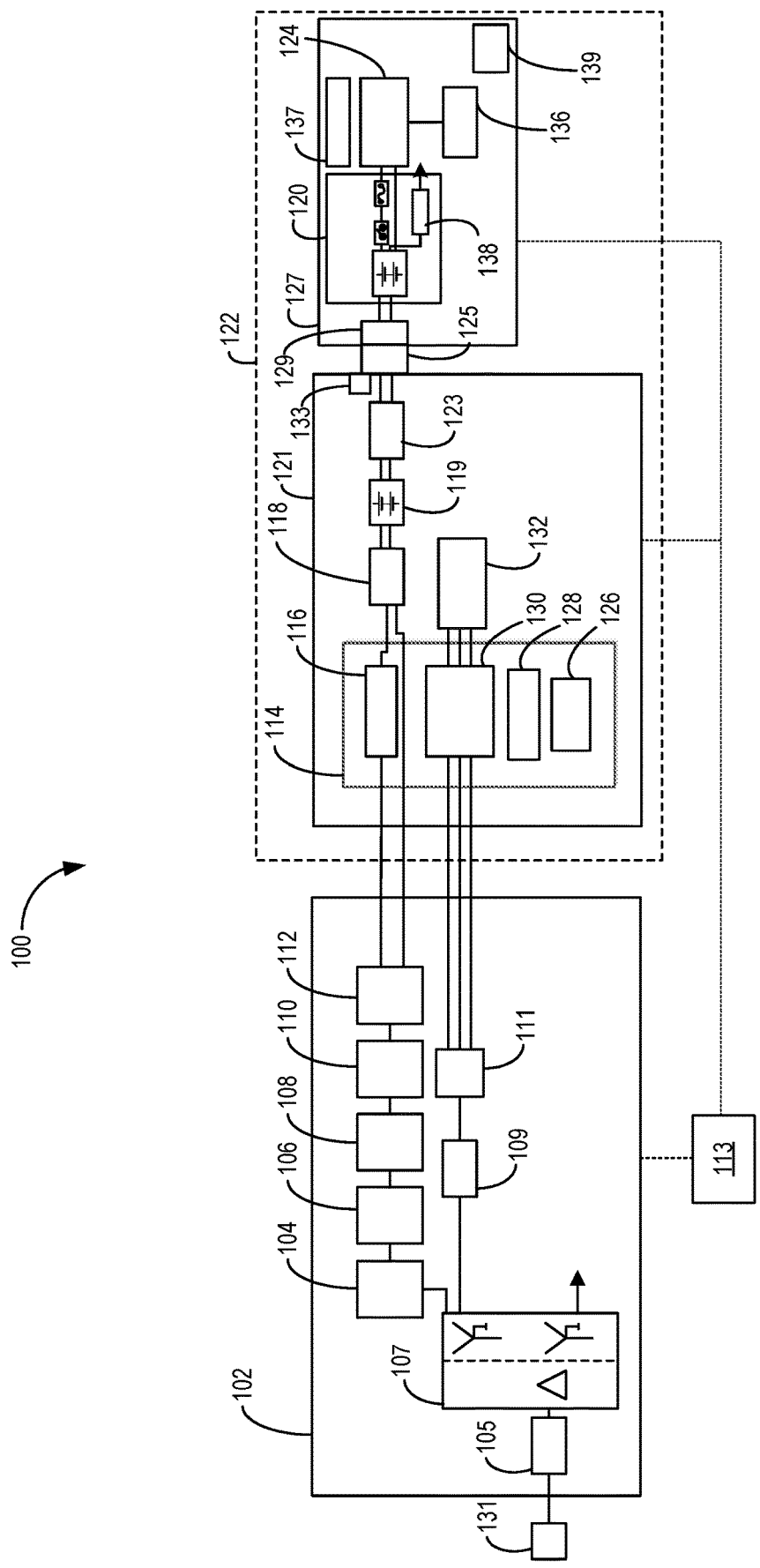
FIG. 1 schematically shows an imaging system including a balanced integrated power source coupled with a rotatable section of a gantry.

Referring to FIG. 1, imaging system 100 is schematically shown. The imaging system 100 in the example shown is a computed tomography (CT) imaging system. However, in other embodiments, the imaging system may be configured for imaging via a different imaging modality (e.g., positron emission tomography (PET), magnetic resonance imaging (MRI), single-photon emission computed tomography (SPECT), hybrid imaging modalities, such as PET/CT, SPECT/CT, etc.).

The imaging system 100 includes a gantry 122 (e.g., a frame or body) and a power distribution unit (PDU) 102. The PDU 102 may include a fuse 104, electromagnetic compatibility (EMC) board 106, soft-start circuit 108, EMC filter caps 110, and/or AC/DC converter 112. The PDU may additionally include a transformer 107, a first circuit breaker 105, a second circuit breaker 109, and a contactor 111. The PDU 102 may be electronically coupled with components of the gantry 122 as shown.

The gantry 122 includes a stationary section 121 (which may be referred to herein as a stationary gantry section) and a rotatable section 127 (which may be referred to herein as a rotatable gantry section and/or rotational portion). The stationary section 121 and the rotatable section 127 are coupled such that the rotatable section 127 is rotatable relative to the stationary section 121. For example, during imaging of a subject (e.g., a patient) by the imaging system 100, the subject may be arranged along a central axis of the imaging system 100 and the rotatable section 127 may rotate around the subject and the central axis for imaging of the subject (e.g., the rotatable section 127 may be configured such that a rotational axis of the rotatable section 127 is coaxial with the central axis). While the rotatable section 127 rotates relative to the stationary section 121, the stationary section 121 does not move (e.g., rotate) relative to a ground surface on which the imaging system 100 sits.

Stationary section 121 of the gantry 122 may include a power pan 114 having a fuse 116, a connector 130, an energy-saving controller 128, and a service outlet 126. Stationary section 121 additionally includes a motor 132 configured to drive (e.g., rotate) the rotatable section 127 (e.g., via a belt). In some embodiments, stationary section 121 may also include a power factor correction (PFC) charger 118 configured to charge stationary power source 119, also located on stationary section 121. In some embodiments the stationary power source 119 (which may be referred to herein as a stationary electrical storage device) may be a battery or array of batteries. PFC charger 118 may draw power from PDU 102 through fuse 116. Stationary power source 119 may be coupled to a charger 123.

Rotatable section 127 of the gantry 122 includes a balanced integrated power source 120, a generator 124, an x-ray tube 136, and an x-ray detector 137. In some embodiments the balanced integrated power source 120 (which may be referred to herein as an integrated power source, integrated electrical storage device, and/or integrated balanced electrical storage device) may be a battery or array of batteries. The integrated power source 120 is integrated to the rotatable section 127 (e.g., directly mounted to the rotatable section 127 and supported by the rotatable section 127). In some embodiments, the integrated power source 120 may be housed within a casing formed by the rotatable section 127. In the embodiments described herein, the gantry 122 is configured without a slip ring. In particular, by configuring the rotatable section 127 to include the balanced integrated power source 120, the x-ray tube 136, generator 124, x-ray detector 137, and other components coupled to the rotatable section 127 may be electrically powered (e.g., energized) by the balanced integrated power source 120 without providing electrical power from components of the stationary section 121 to the x-ray tube 136, generator 124, x-ray detector 137, etc.

The integrated power source 120 may be referred to herein as an electrical storage device (e.g., an integrated balanced electrical storage device) and is integrated with the rotatable section 127. In some embodiments, the integrated power source 120 is mounted directly to the rotatable section 127 (e.g., via fasteners). Mounting the integrated power source 120 to the rotatable section 127 may include fixedly coupling the integrated power source 120 directly to a surface of the rotatable section 127 (e.g., bolting the integrated power source 120 to the surface of the rotatable section 127 and maintaining the position of the integrated power source 120 relative to the rotatable section 127 via the bolts). The integrated power source 120 may be a battery, in some embodiments. Axial servo 132 may be mechanically coupled to rotatable section 127 as shown below with respect to FIGS. 4-5.

Integrated power source 120 may be selectably electronically couplable to a stationary power source 119 via a contactor 125. Selectable coupling refers to controlled coupling of the components, where the components may be coupled or decoupled responsive to operating conditions via electronic controller 113 (described below). For example, as described further below, integrated power source 120 may be electronically coupled to the stationary power source 119 selectably by the controller 113 during some operating conditions of the imaging system 100, and the integrated power source 120 may be electronically decoupled (e.g., electronically isolated) from the stationary power source 119 selectably by the controller 113 during other operating conditions of the imaging system 100. Charger 123 may be arranged between the stationary power source 119 and the contactor 125 and may adjust parameters of electrical energy (e.g., voltage, electrical current, etc.) provided by the stationary power source 119 to the integrated power source 120 via the contactor 125. Integrated power source 120 may be electronically coupled to stationary power source 119 via the contactor 125 by engaging the connector with counterpart contacts 129 of the rotatable section 127. In some embodiments, engagement of the contactor 125 with the counterpart contacts 129 may occur during conditions in which the rotatable section 127 is rotated to a charging position, where the charging position is a pre-defined rotational position of the rotatable section 127 around the central axis. Stationary power source 119 may be charged while PDU 102 is powered on (e.g., energized) via PFC charger 118. The PDU 102 may route (e.g., direct) electrical energy (e.g., electrical current) from an external power source 131 to the stationary power source 119 for charging of the stationary power source 119 (e.g., storage of electrical charge within the stationary power source 119). The external power source 131 may be a power source external to the imaging system, such as an electrical utility source from an electrical wall outlet.

During conditions in which the contactor 125 is engaged with the counterpart contacts 129 (e.g., positioned directly in face-sharing contact with the counterpart contacts 129, with no other components arranged between the contactor 125 and the counterpart contacts 129), stationary power source 119 may provide charging of the integrated power source 120 (e.g., electrical energy may be provided to the integrated power source 120 from the stationary power source 119 through the charger 123, contactor 125, and contacts 129). In some embodiments, an electrical charge capacity of the integrated power source 120 may be configured to provide energization of the x-ray tube 136 and other components coupled to the rotatable section 127 throughout multiple scans of one or more subjects without additional charging of the integrated power source 120. However, as described above, during conditions in which the rotatable section 127 is not rotated and the contactor 125 is engaged with the contacts 129, the integrated power source 120 may be charged by the stationary power source 119. In this way, a size and weight of the integrated power source 120 may be reduced relative to the stationary power source 119 while providing sufficient energization of the components coupled to the rotatable section 127 throughout multiple scans performed by the imaging system 100. A scan of a subject may include acquisition of one or more images of the subject by the imaging system 100, according to the methods described herein. Acquisition of images may include generation of x-ray radiation by the x-ray tube and reception of the x-ray radiation at the x-ray detector, where the x-ray radiation may be attenuated by the body of the subject.

Additionally, by configuring the stationary power source 119 to receive and store electrical energy from the external power source 131, an amount of electrical power consumed by the imaging system 100 may be reduced. In particular, storing electrical energy from the external power source 131 as electrical charge within the stationary power source 119 may reduce a peak electrical power consumption of the imaging system 100 of electrical power provided by the external power source 131. In particular, in other configurations in which the x-ray tube and other components coupled to the rotatable section are energized directly via the external power source 131 (e.g., for generation of x-ray radiation by the x-ray tube during a scan of a subject), a relatively high amount of electrical power may be consumed by operation of the imaging system within a relatively short duration. However, by configuring the imaging system 100 as described herein, a relatively low amount of electrical power may be provided by the external power source 131 to the stationary power source 119 over a longer duration, which may reduce the peak electrical power consumption of the imaging system 100. As a result of reducing the peak electrical power consumption, a cost of the electrical energy provided to the imaging system may be reduced, which may reduce a cost of operation of the imaging system (e.g., relative to configurations in which electrical power is not stored within the stationary power source 119). Further, a rating of fuse 116 may be decreased (e.g., to a 10/20 A fuse) relative to configurations in which electrical power is provided directly to the components coupled to the rotatable section 127 without the stationary power source 119 and integrated power source 120 (e.g., via a slip ring). As a result, a cost of the imaging system may be reduced.

As described above, the integrated power source 120 is coupled to (and supported by) rotatable section 127 of the gantry 122 configured to rotate around a subject to be imaged by the imaging system 100. For example, rotatable section 127 may rotate around a subject during a rotating scan, and because the integrated power source 120 is directly coupled to the rotatable section 127 (e.g., mounted to the rotatable section 127), the integrated power source 120 rotates with the rotatable section 127. Further, generator 124 and x-ray tube 136 are coupled to the rotatable section 127 and rotate with the rotatable section 127 around the imaged subject (e.g., a patient). The integrated power source 120 may be a rechargeable battery (e.g., a lithium-ion battery) or array of batteries, in some embodiments. The integrated power source 120 may be configured to balance the rotation of the rotatable section 127 of the gantry 122 by acting as a counter-weight (e.g., counterbalance) to the generator 124, x-ray tube 136, and/or other components coupled to the gantry 122. In particular, a mass of the integrated power source 120 may counterbalance the combined mass of the x-ray tube 136 and generator 124 during conditions in which the rotatable section 127 is rotated. The integrated power source 120 may be referred to herein as balanced, referring to the balancing of the rotation of the rotatable section 127 by the integrated power source 120. By increasing the balance of the gantry 122 via the integrated power source 120, an imaging quality of the imaging system 100 may be increased and a likelihood of oscillation of the gantry 122 may be reduced, which may decrease a likelihood of degradation of the gantry 122 and/or other components of the imaging system 100.

The integrated power source 120 may additionally provide electrical energy (e.g., electrical current) to other components coupled to the rotatable section 127 of the gantry 122, such as one or more collimators, an onboard rotating processor (ORP), etc. Integrated power source 120 may output 540-600 VDC electrical power to generator 124, in some embodiments. However, other components such as collimators or the ORP may utilize 120 VAC power. As such, integrated power source 120 may include an inverter 138 configured to deliver 120 VAC power to components configured to utilize 120 VAC electrical power.

The imaging system 100 includes electronic controller 113 in electronic communication with PDU 102 and electronic components of the gantry 122. For example, electronic controller 113 may be electronic communication with power pan 114, PFC charger 118, stationary power source 119, charger 123, and contactor 125 arranged at the stationary section 121 of the gantry 122. The electronic controller 113 may additionally be in electronic communication with integrated power source 120, x-ray detector 137, generator 124, x-ray tube 136, and contacts 129 arranged at the rotatable section 127 of the gantry 122. In some embodiments, the electronic controller 113 may be directly electronically coupled to the PDU 102 and/or the electronic components arranged at the stationary section 121 via one or more electrical connectors such as cables. The electronic controller 113 may wirelessly communicate (e.g., send and/or receive data) with the electronic components coupled to the rotatable section 127. For example, the rotatable section 127 may include a wireless communication device 139 configured to be in electronic communication with the electronic controller 113.

The controller 113 receives signals from the various sensors and other electronic components of FIG. 1 and employs the various actuators and other electronic components of FIG. 1 to adjust operation of the imaging system based on the received signals and instructions stored on a memory of the controller. For example, adjusting a rotational position of the rotatable section 127 of the gantry 122 (e.g., to a charging position, similar to the example described below) may include adjusting an energization of the motor 132 configured to drive the rotatable section 127 (e.g., rotate the rotatable section 127). As another example, adjusting a position of the contactor 125 from a disengaged position in which the contactor 125 is not electronically coupled to the counterpart contacts 129 (e.g., the contactor 125 is not arranged directly in face-sharing contact with the counterpart contacts 129 while the contactor 125 is in the disengaged position) to an engaged position in which the contactor 125 is electronically coupled to the counterpart contacts may include energizing an actuator of the contactor 125 (e.g., switch 133) to move the contactor 125 into engagement with the counterpart contacts 129. Other examples are possible.

Referring collectively to FIGS. 2-5, different views of a gantry 200 of an imaging system and an integrated power source 204 are shown. The integrated power source 204 may be referred to herein as a balanced integrated power source 204 and/or integrated balanced electrical storage device. In some embodiments, the integrated power source 204 may be a battery or array of batteries.

Figure 3:
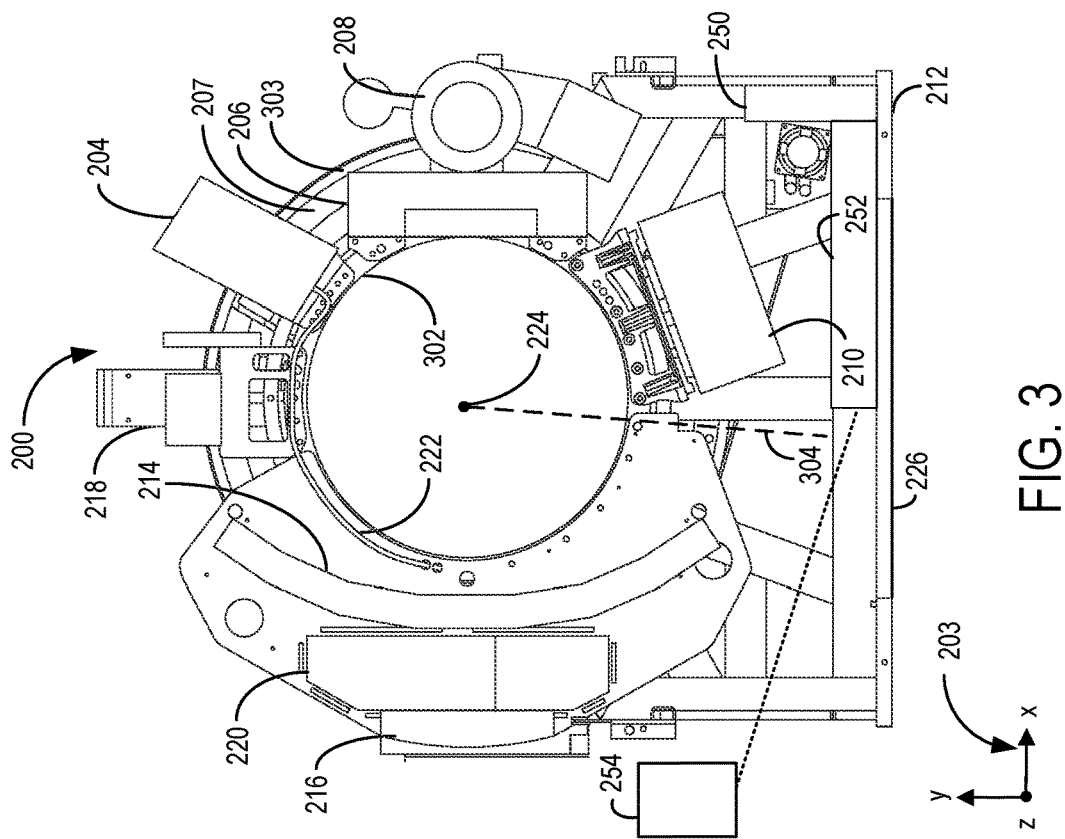
FIG. 3 shows a front view of the gantry of FIG. 2.
Figure 2:
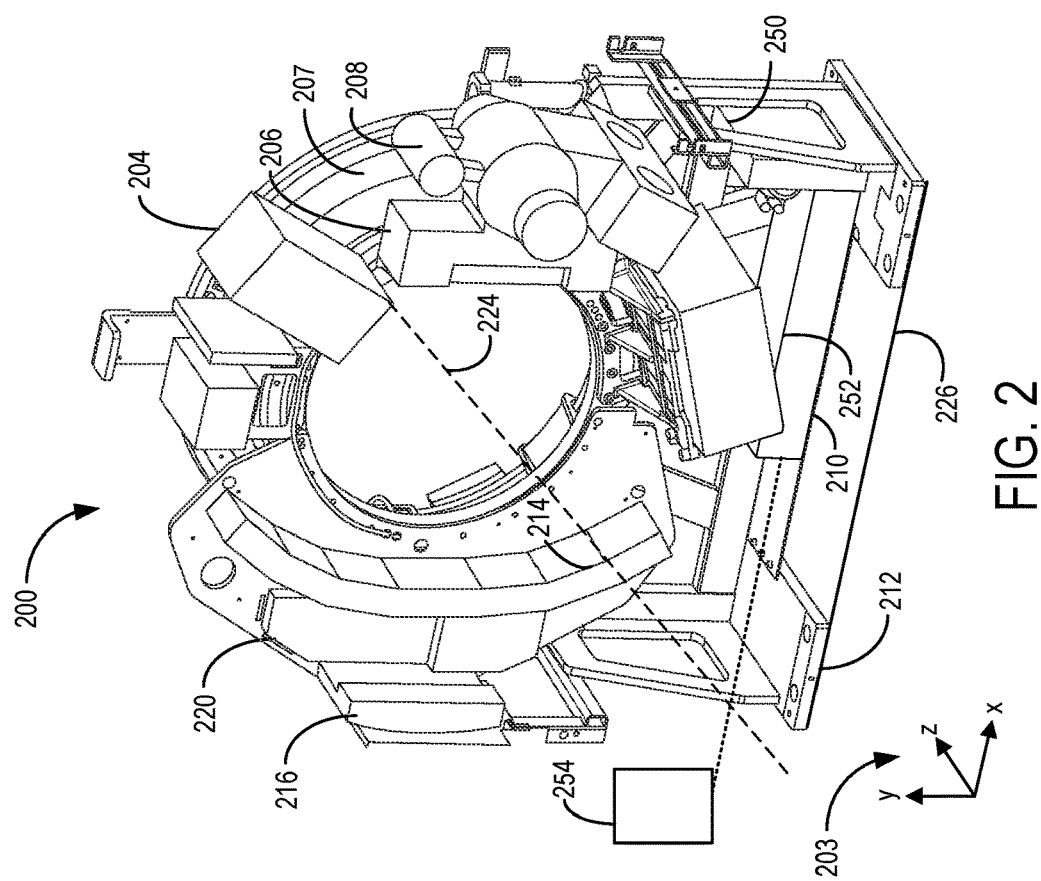
FIG. 2 shows a front perspective view of a gantry of an imaging system including a balanced integrated power source coupled to a rotatable section of the gantry.
Figure 4:
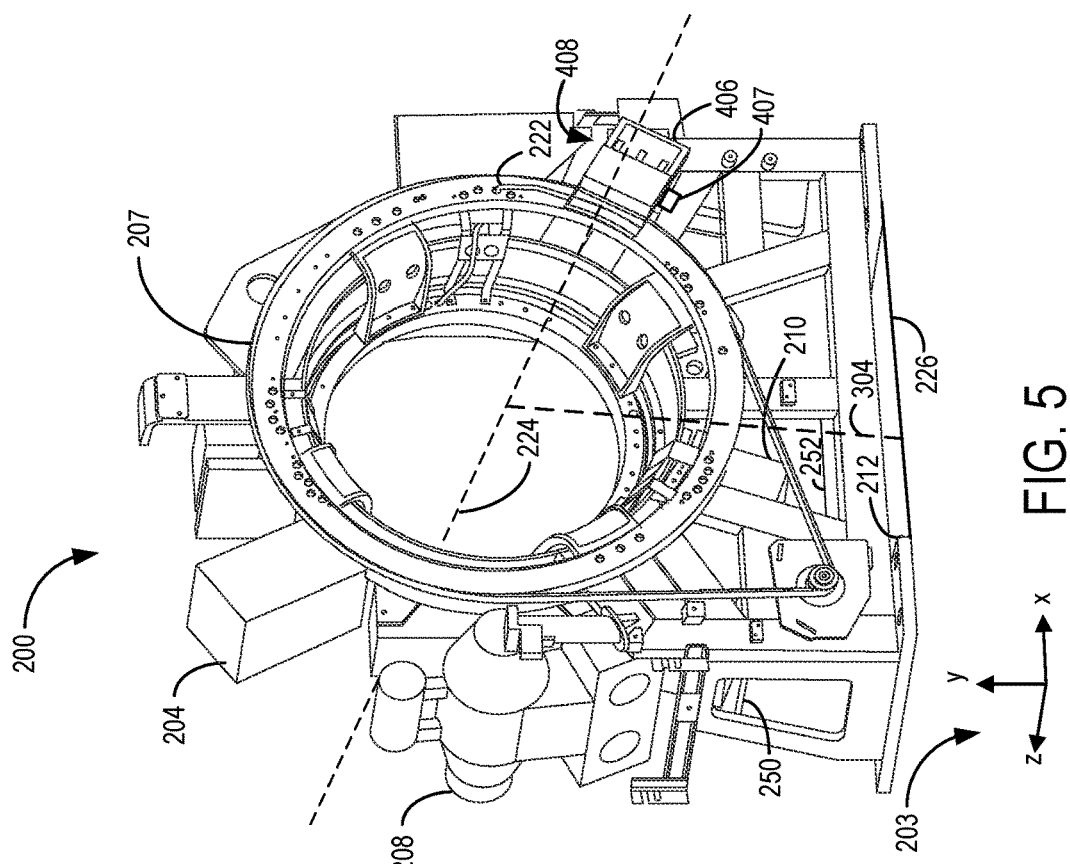
FIG. 4 shows a partially exploded rear perspective view of the gantry of FIGS. 2-3.
Figure 5:
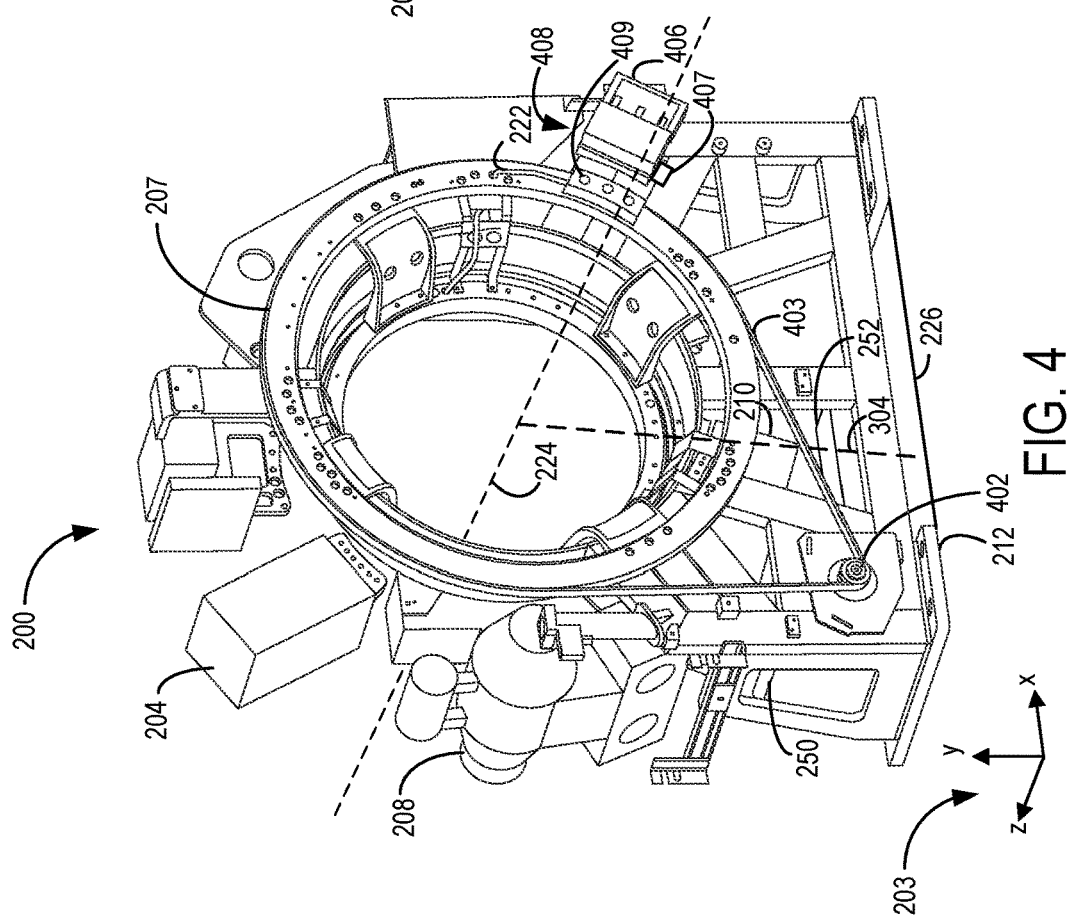
FIG. 5 shows a rear perspective view of the gantry of FIGS. 2-4 in an assembled condition.

FIG. 2 shows a front perspective view of the gantry 200, FIG. 3 shows a front view of the gantry 200, FIG. 4 shows a partially-exploded rear perspective view of the gantry 200, and FIG. 5 shows a rear perspective view of the gantry 200 with the integrated power source 204 coupled to the gantry 200. Reference axes 203 are provided for comparison of the views shown. The gantry 200 and integrated power source 204 may be similar to, or the same as, the gantry 122 and integrated power source 120, respectively, described above with reference to FIG. 1. The imaging system including the gantry 200 may be similar to, or the same as, the imaging system 100 described above with reference to FIG. 1.

As shown by FIG. 2, an x-ray detector 214, an x-ray tube assembly 208, a collimator 206, and a generator 210 are each coupled to, and supported by, a rotatable section 207 of the gantry 200 (which may be referred to herein as a rotatable gantry section and/or rotational portion). Each of the x-ray detector 214, the x-ray tube assembly 208, the collimator 206, and the generator 210 may be electronically coupled to the integrated power source 204 and configured to receive electrical power from the integrated power source 204. The x-ray detector 214, the x-ray tube assembly 208, the collimator 206, and the generator 210 are each electronic devices supported by the rotatable section 207 (e.g., mounted directly to the rotatable section 207) and rotate with the rotatable section 207 while the rotatable section 207 rotates (e.g., during imaging of a subject, such as a patient). The rotatable section 207 may rotate around central axis 224 during a scan of a subject. The integrated power source 204 may be electrically coupled to a charger positioned at a rear side of the gantry 200 via cable 222. The charger may be discussed further with respect to FIG. 4 below. Further, fuse box and power supply assembly (FBPS) 218, wireless communication device 216, and data acquisition system (DAS) 220 may also be coupled to the rotatable section 207 of the gantry 200 and may receive electrical power from integrated power source 204 (e.g., integrated power source 204 may electrically energize the FBPS 218, wireless communication device 216, and DAS 220). Electronic coupling, as described herein, refers to coupling of devices providing transfer of data and/or electrical power between the devices. Electronic coupling may include wireless communications (e.g., electronically coupling wireless communication device 216 with one or more electronic devices at the stationary section 212, such as the controller, a display device, an operator input console, etc., for transfer of data from the wireless communication device 216 to the one or more electronic devices, or vice versa). Wireless communications may include wireless signals, such as WiFi signals. Electronic coupling may further include direct electrical coupling, including coupling of components via an electrical cable, electrical contacts, or other electrically conductive component configured to transmit electricity (e.g., electrical current) between components for energization, data transfer, etc. Electronic decoupling may include electrically separating devices (e.g., by disconnecting the electrical connection between the devices via a switch, directly separating and/or spacing apart electrically conductive components from each other, etc.).

Gantry 200 further includes stationary section 212. Stationary section 212 may be supported by a ground surface 226 on which the gantry 200 sits. The stationary section 212 extends both in front of and behind gantry 200 in the direction of the z-axis of reference axes 201. The rotatable section 207 of the gantry 200 is rotatably coupled to the stationary section 212 such that the stationary section 212 supports the rotatable section 207 vertically above ground surface 226 and the rotatable section 207 is able to rotate relative to the stationary section 212 around axis 224. As the rotatable section 207 rotates relative to the stationary section 212, the stationary section 212 does not move or rotate relative to the ground surface 226.

In the embodiment shown, the gantry 200 is configured without a slip ring. Because the integrated power source 204 is coupled directly to the rotatable section 207, the integrated power source 204 may provide electrical power to the collimator 206, x-ray tube assembly 208, x-ray detector 214, etc. without a slip ring. By configuring the gantry 200 without a slip ring, a cost of the imaging system may be reduced relative to imaging systems that include a slip ring. Additionally, configuring the gantry 200 without a slip ring eliminates potential undesired operation associated with use of a slip ring, such as undesired electronic connection interruptions and potential resulting slip ring degradation. As a result, a reliability of the imaging system may be increased.

Data may be communicated between the components coupled to the rotatable section 207 and components coupled to the stationary section 212 via a bi-directional wireless communication system such as wireless communication device 216. The wireless communication device 216 may be electronically coupled to the integrated power source 204 and may be electrically powered by the integrated power source 204. The wireless communication device 216 may be in electronic communication with DAS 220. Other medical grade RF communication systems, such as a medical implant communication system (MICS) band, or Bluetooth low energy (BLE) communication, may also be included at the rotatable section 207 and electrically powered by the integrated power source 204.

In some embodiments, the integrated power source 204 may provide a first voltage (e.g., 540-600 VDC) to the generator 210 and a second voltage (e.g., 120 VAC) to other components coupled to the rotatable section 207 (e.g., DAS 220, an ORP, the collimator 206, a tube fan, a tube heat exchanger, etc.). In order to provide the different voltages, the rotatable section 207 may include an inverter (such as inverter 138 of FIG. 1) electronically coupled with the integrated power source 204.

As described above, the configuration of the integrated power source 204 may balance the rotatable section 207 to decrease a likelihood of undesired oscillation of the rotatable section 207. In particular, the positioning and weight of the integrated power source 204 relative to the other components coupled to the rotatable section 207 may provide a reduced likelihood of undesired oscillation of the rotatable section 207. As one example, a weight of the integrated power source 204 may be selected to balance the weight of generator 210. In one embodiment, integrated power source 204 may weigh 25 kg. The integrated power source 204 may be coupled to the rotatable section 207 in a position that reduces the likelihood of oscillation of the rotatable section 207 and additionally reduces a length of a cable electronically coupling the integrated power source 204 to the generator 210. In some embodiments, the integrated power source 204 and generator 210 may be positioned at opposite sides of x-ray tube 208 and collimator 206 around a perimeter of the rotatable section 207 (e.g., the x-ray tube 208 may be arranged between the integrated power source 204 and the generator 210 in a circumferential direction of the rotatable section 207). In embodiments in which the integrated power source 204 includes an array of batteries, each battery of the array may be positioned to balance the weight of the generator 210 and other components coupled to the rotatable section 207. Further, in such embodiments, different batteries of the battery array may provide energization of different components coupled to the rotatable section 207. For example, a first battery of the array may provide energization of the x-ray tube 208, a second battery of the array may provide energization of the wireless communication device 216, etc.

X-ray tube 208 and collimator 206 may be coupled to the rotatable section 207 adjacent to each other such that x-rays emitted by the x-ray tube 208 pass through collimator 206. The collimator 206 may collimate the x-ray radiation emitted by the x-ray tube 208. Collimator 206 may be arranged with a first side of the collimator 206 adjacent to inner edge 302 of the rotatable section 207. A second side of the collimator 206, opposite to the first side, may be arranged adjacent to a first side of the x-ray tube 208. A second side of the x-ray tube 208, opposite to the first side of the x-ray tube 208, may extend over an outer edge 303 of gantry 200. X-ray tube 208 may be positioned behind collimator 206 along a radial axis 304 (e.g., toward the outer edge 303 of the gantry 200, with a distance between the collimator 206 and the outer edge 303 in the direction of radial axis 304 being larger than a distance between x-ray tube 208 and outer edge 303 in the direction of radial axis 304).

Detector 214 is arranged opposite to the x-ray tube 208 and the collimator 206 across the central axis 224. X-ray radiation emitted by the x-ray tube 208 through the collimator 206 may interact with a subject positioned along central axis 224 (e.g., the x-ray radiation may be attenuated by the body of the subject) and may be received by the detector 214. Detector 214 may be positioned 180 degrees from the x-ray tube 208 and the collimator 206 in the circumferential direction of the rotatable section 207. Signals (e.g., electronic signals) from detector 214 may be received by DAS 220 and communicated to components arranged at the stationary section 212 (e.g., an operator terminal, display device, etc.) via wireless communication device 216. DAS 220 and wireless communication device 216 may be arranged at outer edge 303 of the rotatable section 207, behind detector 214 in the direction of radial axis 304 from the central axis 224.

A motor 250 is arranged at the stationary section 212 of the gantry 200 and is configured to drive the rotation of the rotatable section 207 responsive to energization of the motor 250 by a stationary power source 252 (or additionally from a power delivery unit, such as PDU 102 described above with reference to FIG. 1) arranged at the stationary section 212. In some embodiments, the stationary power source 252 may be a battery or array of batteries. The stationary power source 252 may be electronically coupled to the motor 250 via a cable or other electrical connection. Motor 250 may be coupled to an axial servo 402 (shown by FIGS. 4-5), with axial servo 402 coupled to the rotatable section 207 via a belt 403. During conditions in which the motor 250 is energized by the stationary power source 252, the motor 250 may drive a rotation of the axial servo 402, and the axial servo 402 may drive a rotation of the rotatable section 207 of the gantry 200 via the belt 403. In this configuration, energization of the motor 250 may result in the rotatable section 207 being driven (e.g., rotated) by the motor 250 via the belt 403 and axial servo 402.

The integrated power source 204 may be charged during conditions in which the rotatable section 207 of the gantry 200 is not rotating, as described further below with reference to the method illustrated by FIG. 6. In some embodiments, the integrated power source 204 may be charged by the stationary power source 252 via a charge assembly 408. The charge assembly 408 includes a contactor 406 and a switch 407 (e.g., a solenoid switch). Switch 407 is shown schematically by FIGS. 4-5. The contactor 406 may be similar to, or the same as, the contactor 125 described above with reference to FIG. 1. The charge assembly 408 is coupled to the stationary section 212 of the gantry 200, and during conditions in which the rotatable section 207 of the gantry 200 is driven (e.g., rotated) by the motor 250, the contactor 406 does not rotate with the rotatable section 207. However, the rotatable section 207 may include counterpart contacts 409 shaped to engage with the contactor 406 during conditions in which the rotatable section 207 is not rotated and is in a charging position (e.g., a pre-defined rotational position of the rotatable section 207 configured to position the counterpart contacts 409 for engagement with the contactor 406). As one example, the charging position may be a position corresponding to zero degrees of rotation relative to an initial position of the rotatable section 207 used while performing a scan of a subject.

While the rotatable section 207 is in the charging position, the contactor 406 may be engaged with the counterpart contacts 409 to electronically couple the stationary power source 252 to the integrated power source 204 via the switch. For example, actuation of the switch may adjust the contactor 406 from a non-engaged position (shown by FIG. 4) to an engaged position (shown by FIG. 5), where, while in the non-engaged position, the integrated power source 204 is not electronically coupled to the stationary power source 252 via the charge assembly 408 (e.g., via the contactor 406), and while in the engaged position, the integrated power source 204 is electronically coupled to the stationary power source 252 via the charge assembly 408. In particular, the contactor 406 may include electrically conductive surfaces that are arranged in direct, face-sharing contact with the electrically conductive counterpart contacts 409 during conditions in which the contactor 406 is in the engaged position. The counterpart contacts 409 may be electronically coupled to the integrated power source 204 via cable 222 as described above, such that electrical energy (e.g., electrical current) may flow from the stationary power source 252 to the integrated power source 204 via the contactor 406, counterpart contacts 409, and cable 222 during conditions in which the contactor 406 is in the engaged position and the rotatable section 207 of the gantry 200 is in the charging position. The solenoid switch may be provided a low voltage (24 VDC) to adjust the contactor 406 from the non-engaged position to the engaged position (or vice versa). In some embodiments, the contactor 406 may move vertically (e.g., along the y-axis) relative to the ground surface on which the gantry 200 sits to engage with the counterpart contacts 409. In other embodiments, the contactor 406 may move horizontally relative to the ground surface to engage with the counterpart contacts 409. In yet other embodiments, the contactor 406 may move in a radial direction relative to the central axis 224 to engage with the counterpart contacts 409.

Stationary power source 252 is configured to receive electrical energy from an external power source 254 (e.g., a power source external to the imaging system including the gantry 200 and the stationary power source 252, such as an electrical utility source from an electrical wall outlet) and the electrical energy provided to the stationary power source 252 by the external power source 254 may be stored within the stationary power source 252 as electrical charge. The external power source 254 is shown schematically by FIGS. 2-3. In some embodiments, the stationary power source 252 may be electronically coupled to the external power source 254 by a cable or other electronic connection. In some embodiments, a PDU, such as the PDU 102 described above with reference to FIG. 1, may electronically couple the stationary power source 252 to the external power source 254. The stationary power source 252 may be configured to automatically disconnect from the external power source 254 during conditions in which an amount of electrical charge stored within the stationary power source 252 exceeds a threshold charge, similar to the example described below with reference to FIG. 6. For example, the stationary power source 252 may be electronically coupled to the external power source 254 via a switch and a cable, where the switch is adjustable from a first position in which the cable provides electrical energy to the stationary power source 252 from the external power source 254 to a second position in which electrical energy does not flow from the external power source 254 to the stationary power source 252 via the cable. However, during conditions in which the stationary power source 254 is disconnected from the external power source 254 as described above, electrical energy from the external power source 254 may continue to be provided to other components at the stationary section 212, such as processor circuitry or boards, fans, power supplies (e.g., transformers), etc.

By charging the integrated power source 204 via the stationary power source 252 during conditions in which the rotatable section 207 of the gantry 200 is not rotating, the rotatable section 207 is in the charging position, and the contactor 406 is engaged with the counterpart contacts 409, the integrated power source 204 may provide energization of the x-ray tube 208, generator 210, and other electronic devices mounted to the rotatable section 207 without a persistent electronic connection between the components mounted to the rotatable section 207 and components external to the rotatable section 207 (e.g., components coupled to the stationary section 212). As a result, the imaging system may perform a scan of a subject without electronic connections between the rotatable section 207 and the stationary section 212 (e.g., without a slip ring electronically coupling the components coupled to the rotatable section 207 to components coupled to the stationary section 212), and a manufacturing cost and/or maintenance cost of the imaging system may be reduced. Further, by configuring the imaging system with both of the integrated power source 204 and the stationary power source 252, the imaging system may provide uninterrupted imaging of a subject during conditions in which the external power source 254 experiences undesired operation (e.g., undesired disconnections or services outages).

The integrated power source 204 may store sufficient electrical charge to provide energization of the components coupled to the rotatable section 207 throughout multiple scans of one or more subjects via various scanning protocols. Charging a device, as described herein, refers to storage of electrical charge within the device (e.g., charging the integrated power source 204 refers to increasing electrical charge stored within the integrated power source 204). The charging of the integrated power source 204 may be controlled via an electronic controller, such as the electronic controller 113 described above with reference to FIG. 1. In some embodiments, an operator of the imaging system (e.g., a technician) may input a command to an input device of the imaging system (e.g., an operator control panel) to request charging of the integrated power source 204. Responsive to the request, the controller may adjust the position of the rotatable section 207 to the charging position via energization of the motor 250, and the controller may additionally adjust the position of the contactor 406 (e.g., via the switch 407) to engage the contactor 406 with the counterpart contacts 409 at the rotatable section 207. In some embodiments, the controller may automatically adjust the rotatable section 207 to the charging position and adjust the contactor 406 to the engaged position responsive to an amount of electrical charge stored within the integrated power source 204 (e.g., responsive to the amount of charge decreasing below a threshold charge). In some embodiments, the controller may automatically adjust the rotatable section 207 to the charging position and adjust the contactor 406 to the engaged position immediately following a scan of a subject by the imaging system responsive to a determination that the scan is completed. In some embodiments, the integrated power source 204 may be charged using a high power charger (e.g., quick charger, fast charger, high powered charging device) so that the amount of time required to charge the integrated power source 204 is minimal to enable the integrated power source to be recharged between scans, particularly between scans of different patients.

In some embodiments, the stationary power source 252 may be charged via regenerative braking of the rotatable section 207. For example, the motor 250 may be configured as a motor/generator and may reduce a rotational speed of the rotatable section 207 following completion of a scan of a subject by converting rotational torque (which may be referred to herein as regenerative braking torque) applied by the rotatable section 207 to the motor 250 to electrical energy. The motor 250 may provide the electrical energy to the stationary power source 252 to increase the amount of electrical charge stored within the stationary power source 252. As one example, the rotatable section 207 may provide regenerative braking torque to the motor 250 via the belt 403, where the rotation of the rotatable section 207 may drive a rotor of the motor 250 to generate electrical energy via regenerative braking.

Figure 6:
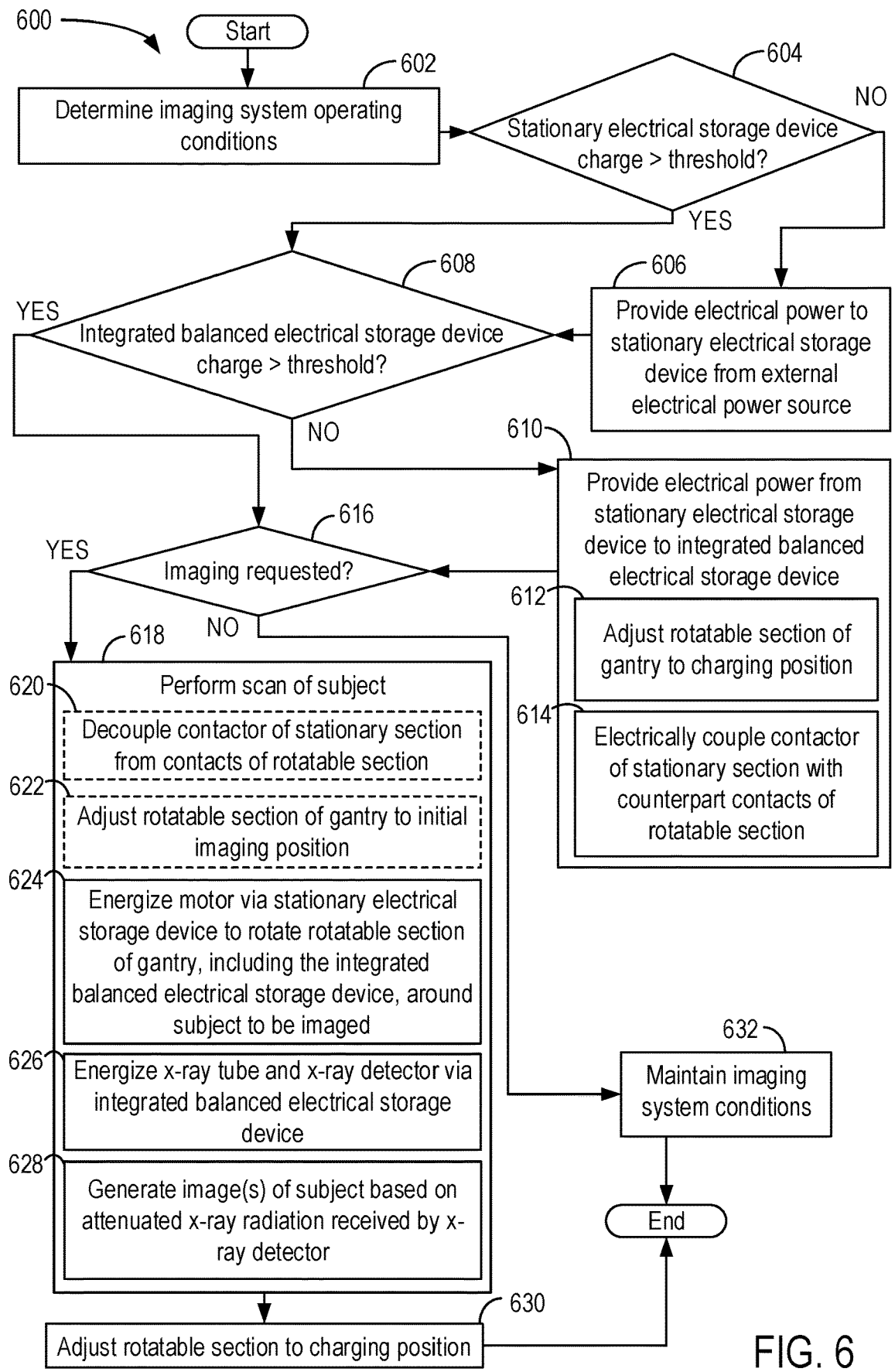
FIG. 6 shows a flow chart illustrating a method for controlling operation of an imaging system including a gantry with a rotatable section including a balanced integrated power source.

Referring to FIG. 6, a flow chart illustrating a method 600 controlling an imaging system including a gantry having a rotatable section with an integrated balanced electrical storage device and a stationary section with a stationary electrical storage device is shown. The imaging system, gantry, rotatable section, stationary section may be similar to, or the same as, the components labeled similarly and described above. The integrated balanced electrical storage device may be similar to, or the same as, the integrated power source 120 described above with reference to FIG. 1 and/or the integrated power source 204 described above with reference to FIGS. 2-5. The stationary electrical storage device may be similar to, or the same as, the stationary power source 119 described above with reference to FIG. 1 and/or the stationary power source 252 described above with reference to FIGS. 2-5. Instructions for carrying out method 600 and the rest of the methods included herein may be executed by a controller (e.g., controller 113 described above with reference to FIG. 1) based on instructions stored on a memory of the controller and in conjunction with signals received from sensors and/or other electronic components of the imaging system, such as the components described above with reference to FIG. 1. The controller may employ actuators of the imaging system to adjust operation of the imaging system, according to the methods described below.

At 602, the method includes determining imaging system operating conditions. Determining the imaging system operating conditions may include determining a rotational position of the rotatable section of the gantry, determining an amount of electrical charge stored within the integrated balanced electrical storage device, determining an amount of electrical charge stored within the stationary electrical storage device, determining a position of a contactor configured to electronically couple the stationary electrical storage device to the integrated balanced electrical storage device, etc. As one example, the rotational position of the rotatable section of the gantry may be determined based on an output of one or more position sensors of the imaging system configured to measure the rotational position of the rotatable section.

The method continues from 602 to 604 where the method includes determining whether a stationary electrical storage device charge is greater than a threshold charge. The stationary electrical storage device charge refers to the amount of electrical charge stored within the stationary electrical storage device. In some embodiments, the threshold charge may be based on a charge storage capacity of the stationary electrical storage device. As one example, the threshold charge may be 70% of the charge storage capacity of the stationary electrical storage device. As another example, the threshold charge may be 80% of the charge storage capacity of the stationary electrical storage device. Other examples are possible. In some embodiments, the threshold charge may be based on a charge storage capacity of the integrated balanced electrical storage device. For example, as described below, the integrated balanced electrical storage device may be charged by the stationary electrical storage device responsive to certain conditions. The threshold charge may be an amount of electrical charge corresponding to a total charge capacity of the integrated balanced electrical storage device, such that determining whether the stationary electrical storage device charge is greater than the threshold charge includes determining whether the stationary electrical storage device charge is at least equal to the total charge storage capacity of the integrated balanced electrical storage device. In this configuration, the controller may determine whether the electrical charge stored within the stationary electrical storage device is a sufficient amount of charge to fully charge the integrated balanced electrical storage device. Other examples are possible.

If the stationary electrical storage device charge is not greater than the threshold charge at 604, the method continues from 604 to 606 where the method includes providing electrical power to stationary electrical storage device from an external electrical power source. Providing the electrical power to the stationary electrical storage device may include electronically coupling the stationary electrical storage device to an external power source to flow electrical energy to the stationary electrical storage device for storage of electrical charge within the stationary electrical storage device. Storing electrical charge within the stationary electrical storage device may be referred to herein as charging the stationary electrical storage device. The external power source may be similar to, or the same as, the external power source 254 shown schematically by FIGS. 2-3 and described above. Electronically coupling the stationary electrical storage device to the external electrical power source may include actuating a switch of the stationary electrical storage device to provide an electrical flow path between the stationary electrical storage device and the external electrical power source. For example, during conditions in which the switch is closed, electrical energy may not flow from the external electrical power source to the stationary electrical storage device, and during conditions in which the switch is opened, electrical energy may flow from the external electrical power source to the station electrical storage device (e.g., via a cable coupling the external electrical power source to the switch). The method then continues from 606 to 608.

While electrical power is provided to the stationary electrical storage device from the external electric power source at 606, electrical energy may be provided to other components arranged at the stationary section of the gantry via the external electric power source, such as a subject support table, one or more controllers, fans, power supplies, and/or other components. Additionally, during conditions in which the stationary electrical storage device charge is greater than the threshold charge at 604, the components arranged at the stationary section as described above may receive electrical energy from the external electric power source. The electrical energy provided to the components at the stationary section by the external power source may be low relative to the electrical energy provided by the stationary electrical storage device to a motor during a scan of a subject (e.g., electrical power provided to the components other than the stationary electrical storage device at the stationary section may be less than 10% of an electrical power provided by the stationary electrical storage device to the motor during a scan of a subject, in some embodiments).

However, if the stationary electrical storage device charge is greater than the threshold charge at 604, the method continues from 604 to 608 where the method includes determining whether the integrated balanced electrical storage device charge is greater than a threshold charge. The integrated balanced electrical storage device charge refers to an amount of electrical charge stored within the integrated balanced electrical storage device. In some embodiments, the threshold charge may be based on a total charge capacity of the integrated balanced electrical storage device. For example, the threshold charge may be 70% of the total charge capacity, 80% of the total charge capacity, etc. In some embodiments, the threshold charge may be based on an expected electrical charge consumption of the imaging system during one or more scans of a subject. For example, the threshold charge may be an amount of charge corresponding to an expected charge consumption of the imaging system in performing two or more scans of a subject, such that during conditions in which the amount of charge stored within the integrated balanced electrical storage device is greater than the threshold charge, the imaging system may perform at least two scans of a subject without fully depleting the electrical charge stored within the integrated balanced electrical storage device. Other examples are possible.

If the integrated balanced electrical storage device charge is not greater than the threshold charge at 608, the method continues from 608 to 610 where the method includes providing electrical power from the stationary electrical storage device to the integrated balanced electrical storage device. The method then continues from 610 to 616.

Providing the electrical power from the stationary electrical storage device to the integrated balanced electrical storage device at 610 includes, at 612, adjusting the rotatable section of the gantry to a charging position. The charging position may be a pre-defined rotational position of the rotatable section of the gantry (e.g., corresponding to 0 degrees of rotation of the rotatable section away from a pre-defined reference location). For example, the charging position may be the position in which the contactor arranged at the stationary section of the gantry is arranged adjacent to, and in alignment with, the counterpart contacts arranged at the rotatable section of the gantry. In this configuration, the contactor may engage with the counterpart contacts while the rotatable section is in the charging position, and during conditions in which the rotatable section is not in the charging position, the contactor does not engage with the counterpart contacts. The rotatable section may be adjusted to the charging position by the controller via energization of the motor configured to drive the rotation of the rotatable section. For example, the controller may energize the motor to rotate the rotatable section to the charging position. The controller may then stop energization of the motor in order to maintain the rotatable section at the charging position.

Providing the electrical power from the stationary electrical storage device to the integrated balanced electrical storage device at 610 includes, at 614, electrically coupling a contactor of the stationary section with counterpart contacts of the rotatable section. Electrically coupling (e.g., electronically coupling) the contactor to the counterpart contacts may include adjusting the contactor from a first position in which the contactor is disengaged from the counterpart contacts (e.g., similar to the example shown by FIG. 4) to a second position in which the contactor is engaged in face-sharing contact with the counterpart contacts (e.g., similar to the example shown by FIG. 5). The contactor may be similar to, or the same as, the contactor 125 shown by FIG. 1 and described above and/or the contractor 406 shown by FIGS. 4-5 and described above. The counterpart contacts may be similar to, or the same as, the counterpart contacts 129 shown by FIG. 1 and described above and/or the counterpart contacts 409 shown by FIG. 4 and described above.

In some embodiments, while electrical power is provided to the integrated balanced electrical storage device by the stationary electrical storage device, electrical power may additionally be provided to the integrated balanced electrical storage device by the external power source. For example, a first portion of electrical power provided to the integrated balanced electrical storage device may originate from the stationary electrical storage device, and a second portion of electrical power provided to the integrated balanced electrical storage device may originate from the external power source. In this configuration, by providing electrical energy to the integrated balanced electrical storage device from both of the stationary electrical storage device and the external power source, the stationary electrical storage device may be configured with a reduced size and/or charge capacity relative to configurations in which the integrated balanced electrical storage device is not provided electrical power by the external power source, which may reduce a cost of the imaging system. The ratio of the amount of electrical power provided by the stationary electrical storage device to the amount of electrical power provided by the external power source (to the integrated balanced electrical storage device) may be based on the electrical power consumption parameters of the imaging system and may be selected to reduce the peak electrical power consumption of the imaging system, similar to the example described above. In some embodiments, greater than 50% of the electrical power provided to the integrated balanced electrical storage device may originate from the stationary electrical storage device.

If the integrated balanced electrical storage device charge is not greater than the threshold charge at 608, the method continues from 608 to 616 where the method includes determining whether imaging is requested. Determining whether imaging is requested may include determining whether a scan of a subject has been requested by an operator of the imaging system (e.g., a technician). For example, the operator may request imaging via input to an operator control console electronically coupled to the controller and one or more display devices. Determining whether imaging is requested may include determining parameters of requested imaging such as scan duration, number of images to be acquired by the imaging system throughout a scan, the anatomy of the subject to be imaged, etc.

If imaging is not requested at 616, the method continues from 616 to 632 where the method includes maintaining imaging system conditions. Maintaining imaging system conditions may include maintaining the rotational position of the rotatable section of the gantry, maintaining the electrical charge stored within the stationary electrical storage device and/or the integrated balanced electrical storage device, maintaining a position of the contactor, etc.

However, if imaging is requested at 616, the method continues from 616 to 618 where the method includes performing a scan of a subject. As one example, the subject may be a medical patient, and the scan may include acquisition of one or more images of the subject via the imaging system as described below. Throughout the scan of the subject, electrical power may be provided from the external power source to components at the stationary section of the gantry. For example, electrical power may be provided to processor circuitry or boards, fans, power supplies (e.g., transformers), a subject support table, etc. In some embodiments, during the scan of the subject, electrical power may be provided to the stationary electrical storage device by the external power source in order to increase the electrical charge stored within the stationary electrical storage device and/or replace electrical charge within the stationary electrical storage device consumed by energization of the motor.

Performing the scan of the subject at 616 may include, at 620, decoupling the contactor of the stationary section from the counterpart contacts of the rotatable section. For example, the controller may energize an actuator of the contactor (e.g., a switch, such as the switch 407 shown by FIGS. 4-5 and described above) in order to move the contactor to disengage the contactor from the counterpart contacts. During conditions in which the contactor is already disengaged from the counterpart contacts at 616, the controller may maintain the contactor in the disengaged position.

Performing the scan of the subject at 616 may include, at 622, adjusting the rotatable section of the gantry to an initial imaging position. In some embodiments, the initial imaging position may be equal to the charging position (e.g., the initial imaging position and the charging position may be a same rotational position of the rotatable section). In other embodiments, the initial imaging position may be rotationally offset from the charging position (e.g., rotationally offset from the charging position by 80 degrees, 90 degrees, etc.). The controller may energize the motor to rotate the rotatable section to the initial imaging position. During conditions in which the rotatable section is already at the initial imaging position at 616, the controller may maintain the rotatable section at the initial imaging position prior to 624.

Performing the scan of the subject at 616 includes, at 624, energizing a motor via the stationary electrical storage device to rotate the rotatable section of the gantry, including the integrated balanced electrical storage device, around the subject to be imaged. Energizing the motor to rotate the rotatable section of the gantry around the subject includes rotating the rotatable section from the initial imaging position around the subject according to imaging parameters input by the operator of the imaging system. For example, the imaging request input by the operator may include a selected number of rotations of the rotatable section around the subject, a selected rotational range of the rotatable section around the subject, etc. The initial imaging position may be a reference position for the requested rotation of the rotatable section around the subject. In some embodiments, energization of the motor may include energization of the motor by both of the stationary electrical storage device and the external power source (e.g., a first portion of electrical energy provided to the motor may originate from the stationary electrical storage device and a second portion of electrical energy provided to the motor may originate from the external power source).

Performing the scan of the subject at 616 includes, at 626, energizing an x-ray tube and an x-ray detector via the integrated balanced electrical storage device. Energizing the x-ray tube and the x-ray detector via the integrated balanced electrical storage device includes providing electrical energy to the x-ray tube for generation of x-ray radiation and providing electrical energy to the x-ray detector for reception of attenuated x-ray radiation passing through the imaged subject. The x-ray tube and x-ray detector may be energized by the integrated balanced electrical storage device without being energized by any other power source (e.g., without being energized by the stationary electrical storage device, external power source, etc.).

Performing the scan of the subject at 616 includes, at 628, generating one or more images of the subject based on attenuated x-ray radiation received by the x-ray detector. For example, the x-ray detector may be in wireless electronic communication with the controller via a wireless communication device (e.g., wireless communication device 139 shown by FIG. 1 and described above, and/or wireless communication device 216 shown by FIG. 2 and described above) and may receive electronic signals from the x-ray detector via the wireless communication device, where the electronic signals are generated by the x-ray detector responsive to reception of attenuated x-ray radiation received by the x-ray detector. The controller may process the electronic signals to generate one or more images of the subject based on the electronic signals.

The method continues from 618 to 630 where the method includes adjusting the rotatable section to the charging position. Adjusting the rotatable section to the charging position may include energizing the motor to rotate the rotatable section to the charging position via the controller.

In this way, by providing the rotatable section of the gantry with the integrated balanced electrical storage device and the stationary section of the gantry with the stationary electrical storage device, performance of the imaging system may be increased. In particular, the integrated balanced electrical storage device may increase a balancing of the rotatable section of the gantry while additionally providing electrical energy to the electronic components mounted to the rotatable section while the rotatable section is rotating. As a result, the imaging system may be configured without additional electromechanical couplings, such as slip rings, configured to provide electrical power from the stationary section to the rotatable section while the rotatable section is rotating. Further, the stationary electrical storage device may provide electrical charging of the integrated balanced electrical storage device while the rotatable section is not rotating, and because the stationary electrical storage device may be electronically decoupled from the external power source during conditions in which the stationary electrical storage device is sufficiently charged, an electrical power consumption of the imaging system may be reduced. As a result, an operation cost, maintenance cost, and/or manufacturing cost of the imaging system may be reduced.

FIGS. 2-5 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

FIGS. 2-5 are shown approximately to scale, although other relative dimensions may be used, if desired.

Note that the example control and estimation routines included herein can be used with various imaging system configurations. The control methods and routines disclosed herein may be stored as executable instructions in non-transitory memory and may be carried out by the control system including the controller in combination with the various sensors, actuators, and other system hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations, and/or functions may be repeatedly performed depending on the particular strategy being used. Further, the described actions, operations, and/or functions may graphically represent code to be programmed into non-transitory memory of the computer readable storage medium in the imaging system, where the described actions are carried out by executing the instructions in a system including the various hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to MRI, PET, and other imaging system types. Moreover, unless explicitly stated to the contrary, the terms "first," "second," "third," and the like are not intended to denote any order, position, quantity, or importance, but rather are used merely as labels to distinguish one element from another. The subject matter of the present disclosure includes all novel and non-obvious combinations and sub-combinations of the various systems and configurations, and other features, functions, and/or properties disclosed herein.

As used herein, the term "approximately" is construed to mean plus or minus five percent of the range unless otherwise specified.

In one embodiment, a method for an imaging system comprises: electronically coupling a motor configured to drive a rotatable section of a gantry to a stationary electrical storage device arranged at a stationary section of the gantry; and electronically coupling an x-ray tube to an integrated electrical storage device mounted to the rotatable section, where the integrated electrical storage device is selectably electronically isolated from the stationary electrical storage device. In a first example of the method, the method further comprises: acquiring a scan of a subject by: energizing the motor via the stationary electrical storage device or an external power source via a power delivery unit to rotate the rotatable section around the subject; and energizing the x-ray tube via the integrated electrical storage device to generate x-ray radiation in a direction of the subject. A second example of the method optionally includes the first example, and further includes: first, electronically decoupling the integrated electrical storage device from the stationary electrical storage device; then, acquiring the scan of the subject; and while acquiring the scan of the subject, maintaining the integrated electrical storage device electronically decoupled from the stationary electrical storage device. A third example of the method optionally includes one or both of the first and second examples, and further includes charging the integrated electrical storage device via the stationary electrical storage device. A fourth example of the method optionally includes one or more or each of the first through third examples, and further includes wherein charging the integrated electrical storage device via the stationary electrical storage device includes: driving the rotatable section via energization of the motor by the stationary electrical storage device to a charging position; and engaging a contactor electronically coupled to the stationary electrical storage device at the stationary section with counterpart contacts electronically coupled to the integrated electrical storage device at the rotatable section. A fifth example of the method optionally includes one or more or each of the first through fourth examples, and further includes: responsive to an electrical charge stored within the integrated electrical storage device increasing above a threshold charge, disengaging the contactor from the counterpart contacts. A sixth example of the method optionally includes one or more or each of the first through fifth examples, and further includes controlling a charging of the stationary electrical storage device by an external power source electronically coupled to the stationary electrical storage device. A seventh example of the method optionally includes one or more or each of the first through sixth examples, and further includes wherein controlling the charging of the stationary electrical storage device by the external power source includes providing electrical energy from the external power source to the stationary electrical storage device based on an electrical charge stored within the stationary electrical storage device. An eighth example of the method optionally includes one or more or each of the first through seventh examples, and further includes wherein the providing of the electrical energy from the external power source to the stationary electrical storage device based on the electrical charge stored within the stationary electrical storage device includes: responsive to the electrical charge decreasing below a threshold charge, flowing electrical current from the external power source to the stationary electrical storage device; and responsive to the electrical charge increasing above the threshold charge, stopping the flow of electrical current from the external power source to the stationary electrical storage device.

In one embodiment, an imaging system comprises: a rotatable gantry section including a first electrical storage device and an x-ray tube driven by the first electrical storage device; and a stationary gantry section including a second electrical storage device and a motor driven by the second electrical storage device to rotate the rotatable gantry section. In a first example of the imaging system, the imaging system further comprises: a contactor mounted to the stationary gantry section and electronically coupled to the second electrical storage device; and counterpart contacts mounted to the rotatable gantry section and electronically coupled to the first electrical storage device. A second example of the imaging system optionally includes the first example, and further includes wherein, while engaged with the counterpart contacts, the contactor electronically couples the second electrical storage device to the first electrical storage device, and while the contactor is disengaged from the counterpart contacts, the second electrical storage device is electronically decoupled from the first electrical storage device. A third example of the imaging system optionally includes one or both of the first and second examples, and further includes wherein an interface of the contactor with the counterpart contacts is the only electronic coupling between the stationary gantry section and electronic devices mounted to the rotatable gantry section. A fourth example of the imaging system optionally includes one or more or each of the first through third examples, and further includes a generator mounted to the rotatable gantry section across from the first electrical storage device, and wherein the x-ray tube is mounted to the rotatable gantry section between the generator and the first electrical storage device. A fifth example of the imaging system optionally includes one or more or each of the first through fourth examples, and further includes wherein a mass of the first electrical storage device mounted to the rotatable gantry section rotationally counterbalances a combined mass of the x-ray tube and the generator mounted to the rotatable gantry section while the rotatable gantry section is rotated by the motor.

In another embodiment, an imaging system comprises: a gantry including a rotatable section and a stationary section; a stationary electrical storage device coupled to the stationary section; a motor electronically coupled to the stationary electrical storage device and configured to rotate the stationary section via energization by the stationary electrical storage device or an external power source feeding a power delivery unit; an x-ray tube, an x-ray detector, and a generator each mounted directly to the rotatable section; and an integrated electrical storage device mounted directly to the rotatable section and configured to counterbalance the x-ray tube, the x-ray detector, and the generator during rotation of the rotatable section. In a first example of the imaging system, the imaging system further comprises a controller with computer readable instructions stored on non-transitory memory that when executed, cause the controller to: acquire a scan of a subject by: energizing the motor via the stationary electrical storage device or the power delivery unit to rotate the rotatable section around the subject to be imaged, while energizing the x-ray tube via the integrated electrical storage device to generate x-ray radiation in a direction of the subject. A second example of the imaging system optionally includes the first example, and further includes instructions stored on the non-transitory memory of the controller that when executed, cause the controller to: electrically charge the integrated electrical storage device while the rotatable section is not rotating by engaging a contactor electronically coupled to the stationary electrical storage device at the stationary section with counterpart contacts electronically coupled to the integrated electrical storage device at the rotatable section; and maintain the integrated electrical storage device electronically decoupled from the stationary electrical storage device while the rotatable section rotates. A third example of the imaging system optionally includes one or both of the first and second examples, and further includes a wireless communication device mounted to the rotatable section in electronic communication with the x-ray detector and configured to wirelessly transmit imaging data from the x-ray detector to an electronic device at the stationary section. A fourth example of the imaging system optionally includes one or more or each of the first through third examples, and further includes wherein the motor is a motor/generator, and further comprising instructions stored on the non-transitory memory of the controller that when executed, cause the controller to: reduce a rotational speed of the rotatable section by providing regenerative braking torque to the motor by the rotatable section; and responsive to receiving regenerative braking torque at the motor; providing electrical energy from the motor to the stationary electrical storage device.

In another embodiment, a method for an imaging system comprises: determining whether an amount of charge of a stationary electrical storage device is greater than a first threshold; determining whether an amount of charge of an integrated balanced electrical storage device is greater than a second threshold; and wherein when the amount of charge of the stationary electrical storage device is greater than the first threshold and the amount of charge of the integrated balanced electrical storage device is greater than the second threshold, responding to commands to perform a scan by energizing a motor electrically coupled to the stationary electrical storage device to rotate a rotational portion of a gantry of the imaging system and subsequently energizing an x-ray tube electrically coupled to the integrated balanced electrical storage device. In a first example of the method, the method further includes: wherein when the amount of the charge of the stationary electrical storage device is below the first threshold, charging the stationary electrical storage device using a power source external to the imaging system. A second example of the method optionally includes the first example, and further includes wherein when the amount of charge of the integrated balanced electrical storage device is below the second threshold, charging the integrated balanced electrical storage device using the stationary electrical storage device. A third example of the method optionally includes one or both of the first and second examples, and further includes wherein charging the integrated balanced electrical storage device using the stationary electrical storage device includes using a high powered charging device. A fourth example of the method optionally includes one or more or each of the first through third examples, and further includes wherein charging the integrated balanced electrical storage device includes energizing the motor to rotate the rotational portion of the gantry so as to align a contactor of one of the stationary electrical storage device and the integrated balanced electrical storage device with corresponding contacts of the other one of the stationary electrical storage device and the integrated balanced electrical storage device. A fifth example of the method optionally includes one or more or each of the first through fourth examples, and further includes electrically coupling the contactor with the corresponding contacts. A sixth example of the method optionally includes one or more or each of the first through fifth examples, and further includes wherein responding to commands to perform the scan further includes decoupling the contactor and the corresponding contacts. A seventh example of the method optionally includes one or more or each of the first through sixth examples, and further includes wherein responding to commands to perform the scan further includes energizing the motor to rotate the rotatable portion of the gantry to an initial imaging position. An eighth example of the method optionally includes one or more or each of the first through seventh examples, and further includes charging the stationary electrical storage device via regenerative braking as the rotational portion of the gantry is slowing after completion of the scan.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for an imaging system, comprising:
electronically coupling a motor configured to drive a rotatable section of a gantry to a stationary electrical storage device arranged at a stationary section of the gantry; and
electronically coupling an x-ray tube to an integrated electrical storage device mounted to the rotatable section, where the integrated electrical storage device is selectably electronically isolated from the stationary electrical storage device;
wherein the integrated electrical storage device electronically couples to the stationary electrical storage device via a contactor of a charging assembly coupled to the stationary section of the gantry and counterpart contacts mounted at a rear side of the rotatable section of the gantry.

2. The method of claim 1, further comprising:
acquiring a scan of a subject by:
energizing the motor via the stationary electrical storage device or an external power source via a power delivery unit to rotate the rotatable section around the subject; and
energizing the x-ray tube via the integrated electrical storage device to generate x-ray radiation in a direction of the subject.

3. The method of claim 2, further comprising:
first, electronically decoupling the integrated electrical storage device from the stationary electrical storage device;
then, acquiring the scan of the subject; and
while acquiring the scan of the subject, maintaining the integrated electrical storage device electronically decoupled from the stationary electrical storage device.

4. The method of claim 1, further comprising charging the integrated electrical storage device via the stationary electrical storage device.

5. The method of claim 4, wherein charging the integrated electrical storage device via the stationary electrical storage device includes:
driving the rotatable section via energization of the motor by the stationary electrical storage device to a charging position; and
engaging the contactor with the counterpart contacts by adjusting the contactor between an engaged positon and a non-engaged position by actuation of a solenoid switch.

6. The method of claim 5, further comprising:
responsive to an electrical charge stored within the integrated electrical storage device increasing above a threshold charge, disengaging the contactor from the counterpart contacts.

7. The method of claim 1, further comprising controlling a charging of the stationary electrical storage device by an external power source electronically coupled to the stationary electrical storage device.

8. The method of claim 7, wherein controlling the charging of the stationary electrical storage device by the external power source includes providing electrical energy from the external power source to the stationary electrical storage device based on an electrical charge stored within the stationary electrical storage device.

9. The method of claim 8, wherein the providing of the electrical energy from the external power source to the stationary electrical storage device based on the electrical charge stored within the stationary electrical storage device includes:
responsive to the electrical charge decreasing below a threshold charge, flowing electrical current from the external power source to the stationary electrical storage device; and
responsive to the electrical charge increasing above the threshold charge, stopping the flow of electrical current from the external power source to the stationary electrical storage device.

10. An imaging system, comprising:
a rotatable gantry section including a first electrical storage device and an x-ray tube driven by the first electrical storage device;
a stationary gantry section including a second electrical storage device and a motor driven by the second electrical storage device to rotate the rotatable gantry section;
a charging assembly coupled to the stationary gantry section, wherein the charging assembly selectively engages with counterpart contacts mounted on an exterior surface of the rotatable gantry section; and
a contactor of the charging assembly electronically coupled to the second electrical storage device;
wherein the counterpart contacts are mounted to a rim of the rotatable gantry section and are electronically coupled to the first electrical storage device; and
wherein the rim is in a plane substantially perpendicular to an axis of rotation of the rotatable gantry section.

11. The imaging system of claim 10, wherein, while engaged with the counterpart contacts, the contactor electronically couples the second electrical storage device to the first electrical storage device, and while the contactor is disengaged from the counterpart contacts, the second electrical storage device is electronically decoupled from the first electrical storage device.

12. The imaging system of claim 11, wherein an interface of the contactor with the counterpart contacts is the only electronic coupling between the stationary gantry section and electronic devices mounted to the rotatable gantry section.

13. The imaging system of claim 10, further comprising a generator mounted to the rotatable gantry section across from the first electrical storage device, and wherein the x-ray tube is mounted to the rotatable gantry section between the generator and the first electrical storage device.

14. The imaging system of claim 13, wherein a mass of the first electrical storage device mounted to the rotatable gantry section rotationally counterbalances a combined mass of the x-ray tube and the generator mounted to the rotatable gantry section while the rotatable gantry section is rotated by the motor.

15. An imaging system, comprising:
a gantry including a rotatable section and a stationary section;
a stationary electrical storage device coupled to the stationary section;
a motor electronically coupled to the stationary electrical storage device and configured to rotate the rotatable section via energization by the stationary electrical storage device or an external power source feeding a power delivery unit;
an x-ray tube, an x-ray detector, and a generator each mounted directly to the rotatable section;
an integrated electrical storage device mounted directly to the rotatable section and configured to counterbalance the x-ray tube, the x-ray detector, and the generator during rotation of the rotatable section; and
counterpart contacts located on a rim of the rotatable section at a rear side of the gantry, wherein the counterpart contacts selectively connect to a charging assembly external to the gantry to charge the integrated electrical storage device.

16. The imaging system of claim 15, further comprising a controller with computer readable instructions stored on non-transitory memory that when executed, cause the controller to:
acquire a scan of a subject by:
energizing the motor via the stationary electrical storage device or the power delivery unit to rotate the rotatable section around the subject to be imaged, while energizing the x-ray tube via the integrated electrical storage device to generate x-ray radiation in a direction of the subject.

17. The imaging system of claim 16, further comprising instructions stored on the non-transitory memory of the controller that when executed, cause the controller to:
electrically charge the integrated electrical storage device while the rotatable section is not rotating by engaging a contactor of the charging assembly with the counterpart contacts, the contactor electronically coupled to the stationary electrical storage device at the stationary section, and the counterpart contacts electronically coupled to the integrated electrical storage device at the rotatable section; and
maintain the integrated electrical storage device electronically decoupled from the stationary electrical storage device while the rotatable section rotates.

18. The imaging system of claim 16, further comprising a wireless communication device mounted to the rotatable section in electronic communication with the x-ray detector and configured to wirelessly transmit imaging data from the x-ray detector to an electronic device at the stationary section.

19. The imaging system of claim 16, wherein the motor is a motor/generator, and further comprising instructions stored on the non-transitory memory of the controller that when executed, cause the controller to:
reduce a rotational speed of the rotatable section by providing regenerative braking torque to the motor by the rotatable section; and
responsive to receiving regenerative braking torque at the motor; providing electrical energy from the motor to the stationary electrical storage device.

20. A method for an imaging system, comprising:
determining whether an amount of charge of a stationary electrical storage device is greater than a first threshold;
determining whether an amount of charge of an integrated balanced electrical storage device is greater than a second threshold;
when the amount of charge of the stationary electrical storage device is greater than the first threshold and the amount of charge of the integrated balanced electrical storage device is greater than the second threshold, responding to commands to perform a scan by energizing a motor electrically coupled to the stationary electrical storage device to rotate a rotational portion of a gantry of the imaging system and subsequently energizing an x-ray tube electrically coupled to the integrated balanced electrical storage device, wherein the integrated electrical storage device is located closer to a collimator of the imaging system than a detector of the imaging system; and
when the amount of charge of the integrated balanced electrical storage device is below the second threshold, charging the integrated balanced electrical storage device using the stationary electrical storage device, wherein charging the integrated balanced electrical storage device includes energizing the motor to rotate the rotational portion of the gantry so as to align a contactor of one of the stationary electrical storage device and the integrated balanced electrical storage device with corresponding contacts of the other one of the stationary electrical storage device and the integrated balanced electrical storage device at a lower half of a rear side of the gantry.

21. The method of claim 20, further comprising, when the amount of the charge of the stationary electrical storage device is below the first threshold, charging the stationary electrical storage device using a power source external to the imaging system.

22. The method of claim 20, wherein charging the integrated balanced electrical storage device using the stationary electrical storage device includes using a high powered charging device.

23. The method of claim 20, further comprising electrically coupling the contactor with the corresponding contacts.

24. The method of claim 23, wherein responding to commands to perform the scan further includes decoupling the contactor and the corresponding contacts.

25. The method of claim 20, wherein responding to commands to perform the scan further includes energizing the motor to rotate the rotatable portion of the gantry to an initial imaging position.

26. The method of claim 20, further comprising charging the stationary electrical storage device via regenerative braking as the rotational portion of the gantry is slowing after completion of the scan.

* * * * *